(12) United States Patent
Wolf et al.

(10) Patent No.: US 9,500,461 B2
(45) Date of Patent: Nov. 22, 2016

(54) METHOD FOR QUANTIFYING CORROSION AT A PRESSURE CONTAINING BOUNDARY

(71) Applicant: ExxonMobil Research and Engineering Company, Annandale, NJ (US)

(72) Inventors: Henry Alan Wolf, Morristown, NJ (US); Alan M. Schliowitz, Highland Park, NJ (US); Manuel S. Alvarez, Warrenton, VA (US); Anastasios Skoulidas, Bristow, VA (US); David Samuel Deutsch, Beaumont, TX (US); Katie Walker, Milford, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 619 days.

(21) Appl. No.: 13/710,581

(22) Filed: Dec. 11, 2012

(65) Prior Publication Data

US 2013/0191038 A1    Jul. 25, 2013

Related U.S. Application Data

(60) Provisional application No. 61/570,454, filed on Dec. 14, 2011.

(51) Int. Cl.
*G01B 5/00* (2006.01)
*G06F 17/10* (2006.01)
*G01N 17/04* (2006.01)

(52) U.S. Cl.
CPC ............... *G01B 5/00* (2013.01); *G01N 17/04* (2013.01); *G06F 17/10* (2013.01)

(58) Field of Classification Search
CPC .............................. G06F 17/00; G01B 5/00
USPC .............................................. 702/34
See application file for complete search history.

(56) References Cited

U.S. PATENT DOCUMENTS

| | | | |
|---|---|---|---|
| 4,945,758 A * | 8/1990 | Carpenter ............. | G01N 17/00 73/86 |
| 7,681,449 B2 | 3/2010 | Wolf et al. | |
| 8,521,445 B2 * | 8/2013 | Snelling et al. ............. | 702/34 |
| 2007/0199379 A1 * | 8/2007 | Wolf et al. ............. | 73/590 |
| 2008/0141780 A1 * | 6/2008 | Wavering et al. ............. | 73/723 |
| 2012/0099097 A1 * | 4/2012 | Coupe et al. ............. | 356/32 |

OTHER PUBLICATIONS

PCT Search Report issued in corresponding PCT Application No. PCT/US2012/069156, dated Mar. 5, 2013 (3pgs.).
PCT Written Opinion issued in corresponding PCT Application No. PCT/US2012/069156, dated Mar. 5, 2013 (5 pgs.).
K.D. Efird et al., "Correlation of Steel Corrosion in Pipe Flow With Jet Impingement and Rotating Cylinder Tests", Corrosion 49 (1993), pp. 992-1003.

* cited by examiner

*Primary Examiner* — Manuel L Barbee
(74) *Attorney, Agent, or Firm* — Glenn T. Barrett; Andrew T. Ward (57) ABSTRACT

A method for determining the amount and rate of corrosion which has occurred on the surface of a process unit by measuring corrosion with a corrosion sensor and measuring at least one parameter inside the process unit. Corrosion on the internal surfaces of a process unit can then be determined.

7 Claims, 7 Drawing Sheets

Resonance frequency of tuning fork mechanical oscillator in water prior to any mass loss: 869 Hz.

Figure 4A

A. Relationship for the Figure 3A Data for Less than 200mg of Mass Loss

Figure 4B

B. Relationship for Similarly Fabricated Mechanical Oscillator

Figure 5

Resonance frequency of tuning fork mechanical oscillator in water prior to any mass loss: 869 Hz.

Circled data point was collected during the test for the data shown in Figure 6

Figure 8

Circled data point was collected during the test for the data shown in Figure 6

Figure 9

Circled data point was collected during the test for the data shown in Figure 6

Figure 10a

Wall shear stress on pipe wall downstream of mechanical oscillator

Figure 10b

Wall shear stress at pipe elbow

METHOD FOR QUANTIFYING CORROSION AT A PRESSURE CONTAINING BOUNDARY

FIELD OF THE INVENTION

The present invention generally relates to a method for determining corrosion. In particular, the method corresponds to a device that measures corrosion of the process containing vessels and piping of a petroleum unit in a refinery or other industrial process. Methodology is disclosed to provide an absolute determination of the metal loss of the pressure containing boundary and/or internally mounted components inside the process equipment based on the sensor output.

BACKGROUND OF INVENTION

Corrosion is a significant problem in petroleum refineries and other industrial plants which process corrosive materials. Corrosion can cause deterioration of valves, gauges and other equipment. Corrosion can also cause leaks with large environmental and financial costs.

Various sensors can be used to monitor corrosion. Typically a sensor will be connected to a display which can be monitored to determine the relative corrosion rate which has occurred to the pressure containment system. The most common areas of corrosion concern in the pressure containment boundary are at the interior wall of a pipe or vessel.

Alternatively, models can be used to predict the level of corrosion from known plant operating parameters. For example, predictive corrosion models exist for estimating corrosion levels from operating temperature, flow conditions and composition of the liquid inside the plant operating unit.

Based on either a sensor or a corrosion model, the plant operator can take action if the corrosion rate has reached an excessive level. For example, the operator might choose to reduce throughput, change process conditions, or shut down the process or use corrosion inhibiting chemicals.

Typically, corrosion sensors are fabricated out of a corroding material and corrosion is monitored by measuring the amount of corrosion or corrosion rate which has occurred on the sensor itself. However, one really wants to know how much corrosion has occurred on the equipment being monitored. For example, in the case of a pipe or reactor vessel, one might want to know how much corrosion or corrosion rate that has occurred on the wall of the pipe or reactor vessel.

Typically, corrosion sensors measure the relative amount of corrosion that has occurred. For example, a corrosion sensor might be able to determine that the corrosion rate has increased. However, it is even more preferable to know the absolute level of corrosion or corrosion rate that has occurred to a process unit—for example on a pipe wall.

The present invention is a method for determining the amount of corrosion which has occurred on the interior of a process unit from the amount of corrosion information which is measured on a sensor. As part of the methodology, this invention also devises a measurement protocol to relate the sensor output to its metal loss. Consequently, this invention provides the necessary method of calibrating the output of the corrosion sensor to metal loss on the process containment equipment such a pipes and vessels.

SUMMARY OF INVENTION

The present invention is a method for determining the amount of corrosion that occurred on the interior of piping or a process unit in a refinery. Examples of refinery process units include crude units, vacuum crude units, deasphalters, solvent extractors, hydrocrackers, catalytic crackers, visbreakers, cokers, hydrofiners, reformers, hydrofiners, hydrotreaters, and alkylation units. The method includes determining the amount of metal loss or metal loss rate of a corrosion sensor which then allows the determination of corrosion on at least one point on the interior surface of a process unit of a plant.

The method includes the steps of quantifying the amount of corrosion that occurred on a corrosion sensor that is in contact with the fluid inside the process unit and relating that corrosion to the corrosion on the inside surface of the process unit.

In one embodiment, the corrosion of the corrosion sensor is related to the corrosion of the wall by computational fluid dynamic (CFD) modeling using wall shear stress. In another embodiment, the corrosion rate of the corrosion sensor is related to the corrosion of the process equipment using a coupon fixed to the interior wall of a flow loop or the process unit itself.

In a preferred embodiment, the corrosion sensor is the mechanical oscillator disclosed in U.S. Pat. No. 7,681,449.

DESCRIPTION OF THE PREFERRED EMBODIMENT

The present invention relates the corrosion of a metal loss sensor to the corrosion on the wall of a refinery process unit due to the corrosive fluid inside the unit. Electrical resistance (ER) and linear polarization resistance (LPR) sensors are compatible with the present invention. More preferably, the metal loss sensor will be similar to the mechanical oscillator described in U.S. Pat. No. 7,681,449. The relationship may be made by computational fluid dynamics (CFD) modeling or by comparing the corrosion of the oscillator to the corrosion of a section of the interior wall of the process unit. Although mechanical oscillator, LPR, and ER sensors can accommodate the CFD approaches described herein, the only the mechanical sensor is most suitable where direct weight loss measurements of the sensor are used.

Figure 1:
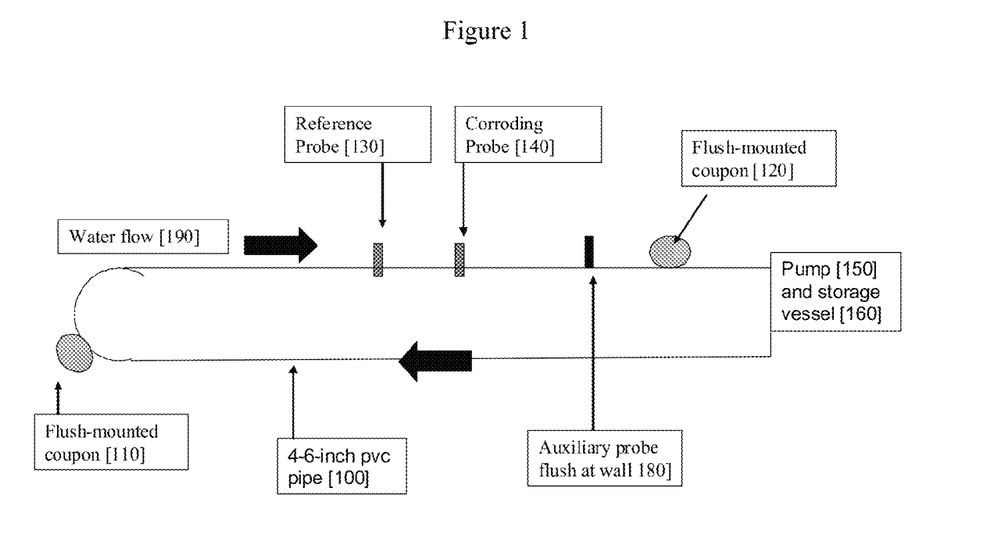
FIG. 1 illustrates a flow loop test set-up to enable the measurement of the metal loss sensor compared to metal loss at the pipe wall.

FIG. 1 shows an example of a flow loop testing apparatus that can be used to conduct the calibration of the metal loss sensor. This calibration relates the oscillator rate of frequency change to the corrosion rate of the mechanical oscillator and ultimately to the corrosion rate of the pressure containing item such as a pipe wall. The flow test facility is used to house the metal loss sensor and flush mounted coupons. To the extent possible, the corrosion conditions in the fluid of the flow test facility should be consistent with the corrosion conditions in the service fluid of interest. Most preferably, the flow test facility can be a part of the actual service to be monitored by the metal loss sensor. In cases where the use of an off-line flow test facility is used, the flow conditions and the formation of corrosion scale that may retard or enhance subsequent corrosion should be consistent with the service fluid of interest.

The FIG. 1 flow test facility consists of pipe [100]. For the case shown in FIG. 1, the pipe is plastic 4 inches diameter. The overall length of each straight section is approximately 40 feet and the length of the elbow section is approximately 4 feet. The precise construction materials, dimensions, and details are not critical to the practice of the calibration methodology described herein. The facility needs to accommodate at least 1 metal loss coupon that can be removed and weighed as part of the calibration process. FIG. 1 shows two coupons: one located in an elbow section [110] and on in a straight section [120]. The loop shown in FIG. 1 has provisions for both a reference non-corroding reference probe [130] and corroding probe [140], the metal loss sensor. Optionally, provisions can be made for other auxiliary probes [180] that can also be evaluated during the testing. Other support components such as a pump and storage vessel [150, 160] are also shown. The FIG. 1 test facility is designed to operate at ambient temperature with water [190] flow.

Figure 2:
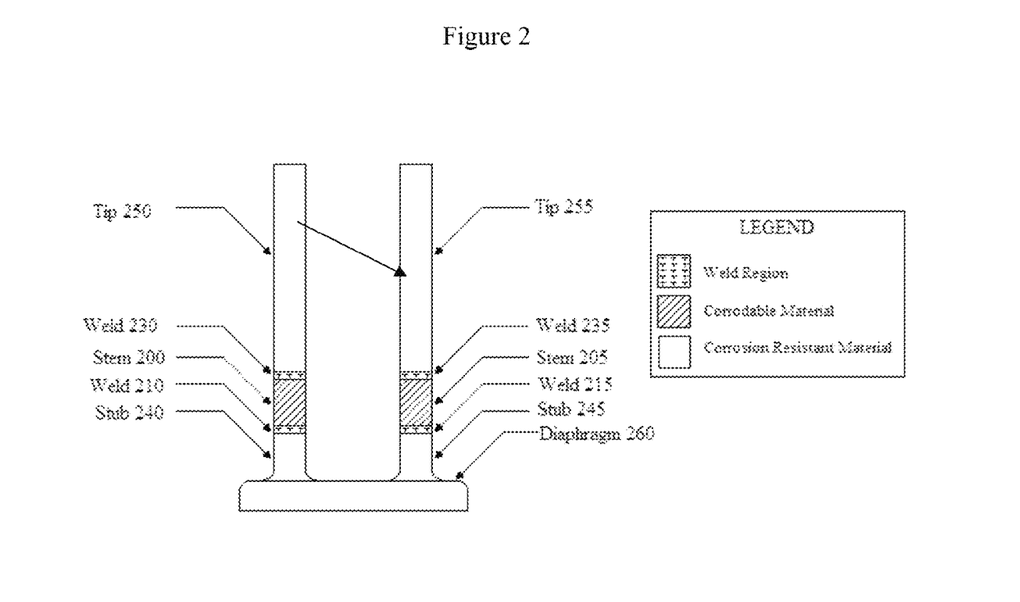
FIG. 2 shows a mechanical oscillator corrosion probe that is used as an example to demonstrate the principles herein.

To illustrate the calibration process, the mechanical oscillator metal loss sensor of U.S. Pat. No. 7,681,449 and as shown in FIG. 2 is used as an example. In U.S. Pat. No. 7,681,449 it is shown that metal loss from corrodible stem elements [200, 205] cause the frequency of the oscillator to be reduced. The corrodible stems are welded in the tine between the tips [250, 255] and the stubs [240, 245]. Welds [210, 215, 230, 235] make the connection between the corrodible stem and the tip or the stub. The tine is the fully assembled structure of the tip, stem, and stub. Each tine connects to the diaphragm [260]. Typically, all the materials of the wetted elements of the tuning fork corrosion probe (except the corrodible stem) are high alloy materials compatible with the process fluid.

Figure 3:
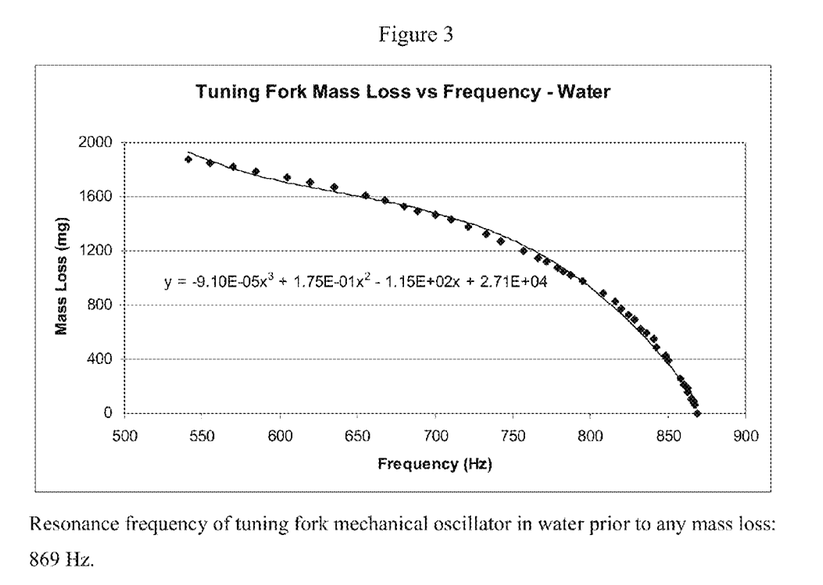
FIG. 3 presents the mass loss of a mechanical oscillator metal loss sensor under static no flow conditions as a function of its frequency change as measured in water.

FIG. 3 shows the change in mass loss from corrodible elements [200, 205] as a function of the oscillator resonance frequency. The exact mechanism to achieve the mass loss is not critical—it can either be chemical or mechanical. In the case of FIG. 3 mass loss at each step was achieved in a bench-top laboratory set-up, not a flow loop, by using a 10-15% solution of sulfuric acid for a period of 1-3 days. To prevent any mass loss of the stainless steel components shown in FIG. 2 diaphragm, stubs, and tips [260, 240, 250, 245, 255], wax was used to mask those sections during the exposure to sulfuric acid. After the acid exposure, the metal loss sensor was cleaned (wax removed), dried, and weighed. Its resonance frequency in air and water were measured after each metal loss step. Conducting these metal loss and measurement steps iteratively enable the correlation of metal loss to resonance frequency. FIG. 3 shows the relationship between the sensor resonance frequency measured in water and its mass loss. For corrosion sensors such as ER and LPR probes that do not have corrodible elements amenable for direct weight loss measurement, a surrogate coupon can be utilized to measure corrosion rate.

Employing the density and dimensions of the corrodible element, it is possible to convert the weight loss measurements of FIG. 3 to the radial thickness reduction of the corrodible element using the following formula (for a corrodible element with a cylindrical shape):

$$R_0 = \sqrt{M_0/(\pi \rho L)}$$  Equations 1

$$R_0 - R_1 = (\sqrt{M_0} - \sqrt{M_1})/(\pi \rho L)^{0.5}$$

Where
$R_0$=radius of corrodible elements prior to corrosion (mm)
$R_1$=radius of corrodible after corrosion results in new (reduced) mass $M_1$ (mm)
$R_0 - R_1$=radius change of corrodible element after mass loss of $(M_0 - M_1)$ (mm)
$M_0$=initial mass of corrodible elements (mg)
$M_1$=new (reduced) mass of corrodible elements (mg)
L=length of corrodible elements (mm)
$\rho$=density of corrodible elements (mg/mm$^3$)

Figure 5:
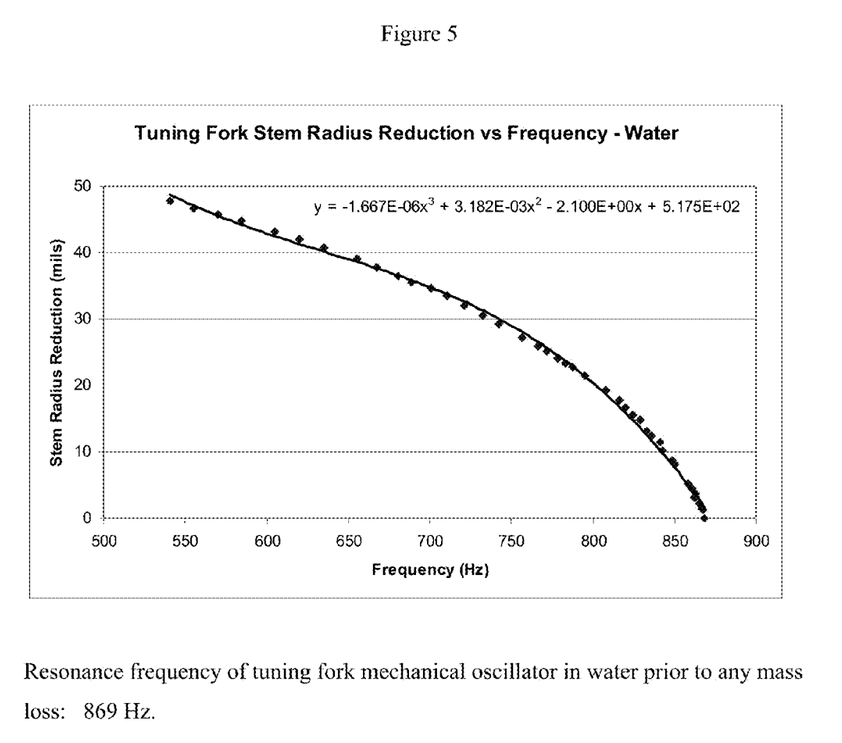
FIG. 5 converts the mass loss vs. frequency change results shown in FIG. 3 to the thickness change of the mechanical oscillator corrodible element vs. frequency change.

For carbon steel (density=7.7 mg/mm$^3$), length=7.3 mm, Mo=2730 mg (for initial radius of 2.75 mm), FIG. 5 plots the frequency change of FIG. 3 compared to the change of the radius of corrodible elements [200,205]. The radii reductions of FIG. 5 correspond to the mass losses of FIG. 3.

The mechanical oscillator used to generate the information in FIGS. 3 and 5 was essentially corroded to failure. However, applying consistent fabrication and assembly methodologies, it is possible to construct mechanical oscillators that have similar frequency change per unit mass loss. Although there may be a slight offset in the absolute resonance frequency of the oscillators prior to any mass loss, the shapes of the curve (in particular their first derivatives) are virtually identical. This observation enables use of the data in FIGS. 3 and 5 as calibrations for other mechanical oscillators that have been similarly constructed. The example that follows demonstrates how the data of FIG. 5 are used to determine corrosion rate for another similar mechanical oscillator metal loss sensor.

Figure 4A:
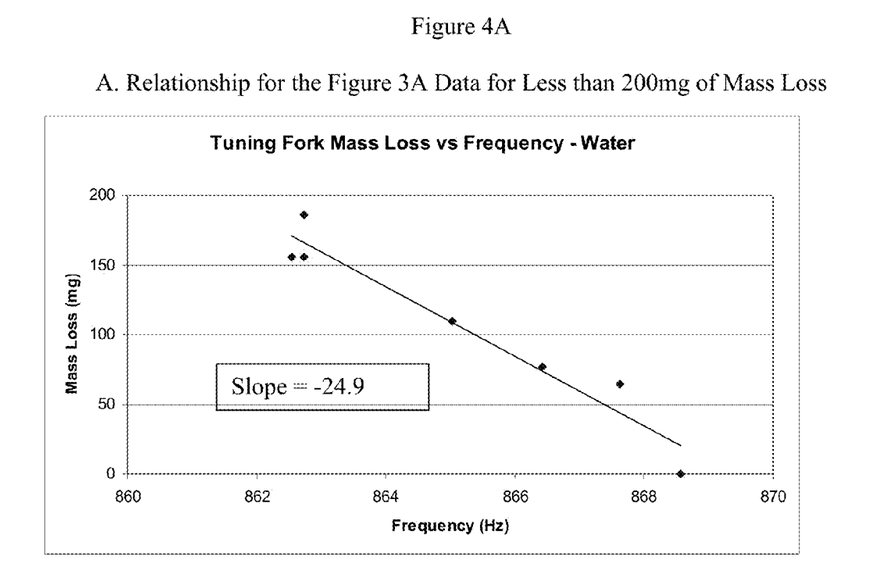
FIGS. 4a and 4b compares the frequency and mass changes of two mechanical oscillator metal loss sensors under the same conditions used for making the FIG. 3 measurements.
Figure 4B:
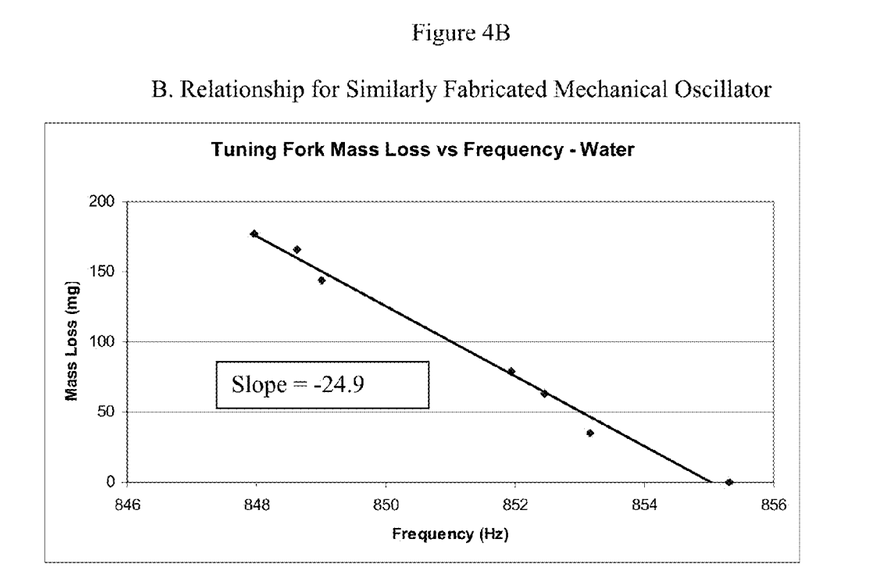

In some cases, it may be desirable to confirm that the shape of the frequency vs. mass loss curve of a new mechanical oscillator is similar to the calibration oscillator that was used to generate the FIG. 3 results. This confirmation can be accomplished by removing a limited amount of mass. A controlled mass removal can be accomplished mechanically or chemically which does not require a flow loop. This approach leaves most of the corrodible element available for use in the intended environment. FIGS. 4a/b show the mass loss curves for two similarly constructed tuning fork corrosion probe oscillators. One set of data in FIG. 4a is a re-plotting of the FIG. 3 results for a mass loss up to 200 mg. The other FIG. 4b plot presents similar data from a separate mechanical loss oscillator that has the same design as the oscillator used for FIG. 3. Since the slopes of both sets of FIG. 4a/b data are the same, their mass loss per unit frequency change are the same.

A step in this procedure is to compute the sensitivity of the metal loss sensor from the data in FIG. 5. The sensitivity is determined by the metal loss thickness change per unit of frequency change. In the case of FIG. 5, that parameter is the first derivative of those data which provides the slope of the data at each point along the curve in the units of mils per Hz. The resulting equation is:

$$S = -5 \times 10^{-6} f^2 + 0.006364 f - 2.1 \quad \text{Equation 2}$$

Where

S=sensitivity of probe (change in thickness loss per unit frequency): (mils/Hz)

f=average frequency of mechanical resonator during the measurement: (Hz)

Figure 6:
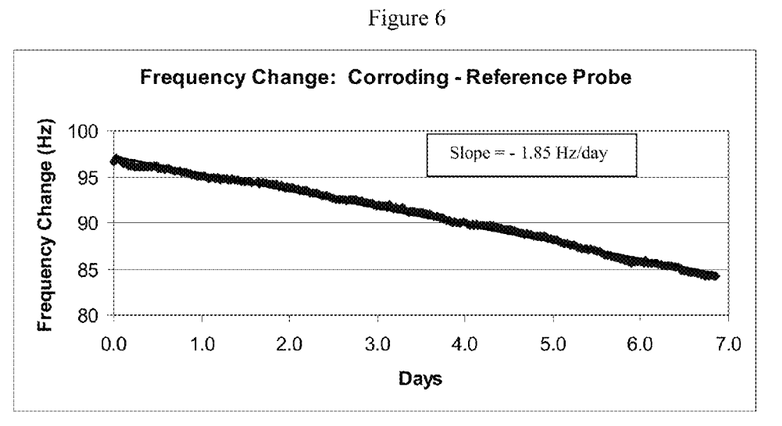
FIG. 6 shows the frequency change of a mechanical oscillator metal loss sensor under flowing conditions in a corrosive fluid as function of time.

FIG. 6 shows the results of another mechanical oscillator of the type shown in FIG. 2 that was installed in the flow loop shown in FIG. 1. For this 7 day test with circulating water, the flow rate was 1.8 ft/sec, pH ranged 5.5-8.5, with an average temperature range of 71-77 degrees Fahrenheit, and oxygen content was maintained in the range of 0.5-2.0 ppm. As described in U.S. Pat. No. 7,681,449, a reference non-corroding mechanical oscillator was also installed in the flow loop. The resonance frequency of both mechanical oscillators was measured at approximately 30 minute intervals. The FIG. 6 data are derived from the resonance frequency subtraction of the reference mechanical oscillator from the corroding oscillator. As shown in FIG. 6, the average slope of the net frequency reduction is −1.85 Hz per day. Maintaining reasonably constant process conditions during the 7-day test results in a constant slope of the frequency change over time.

Equation 2 enables the conversion of the FIG. 6 rate of frequency change (−1.85 Hz per day) into a corrosion rate. At the start of data collection, day 0 in FIG. 6 when flow is initiated in the loop, the mass loss sensor had previously lost 11 Hz during other testing. During the FIG. 6 testing, the mechanical oscillator resonance frequency dropped an additional 13 Hz. That makes the average frequency for use in Equation 2 equal to 17.5 Hz (11+13/2). Dividing the frequency change by 2 provides a simple average frequency change during the multi-day test. Substituting 869−17.5=851.5 Hz into Equation 2 (as a measure of the average frequency) results in a probe sensitivity of S=−0.30 mil/Hz, where 1 mil equals 0.001 inch. The corrosion rate as measured by the probe is equal to:

$$\text{Corrosion rate at probe} = -0.30(\text{mil/Hz}) \times -1.85(\text{Hz/day}) \quad \text{Equation 3}$$

$$= 0.567 \text{ mil/day or}$$

$$= 0.567(\text{mil/day}) \times 365(\text{days/year})$$

$$= 207 \text{ mils/year(mpy)}$$

Additional information is available to validate the calibration results demonstrated by Equation 3. In addition to measuring the resonance frequency of the probe during the FIG. 6 data collection, it was also possible to measure the weight loss of the probe [140] and flush mounted coupon [120] shown in FIG. 1. The mass of the probe and coupon were individually measured prior to starting the FIG. 6 testing and at the conclusion of the test. In accord with measuring, preparation, and calculation procedures of ANSI G1-03 (Standard Practice for the Preparation, Cleaning, and Evaluating Corrosion Test Specimens), the average corrosion rates of the probe and coupon are computed and subsequently graphed in FIG. 7. All of the FIG. 7 corrosion rate data are determined using weight loss. The flat circular coupon, diameter of 0.625 inch, is fabricated from the same steel as the corrodible element of the mechanical oscillator. The flat, circular face of the coupon is exposed to the flow. The edge of the coupon is treated with paint, Teflon®, or other material that prevents corrosion in the water flow environment. Therefore, the corrosion rate of the coupon provides a reasonable estimate of the corrosion at the pipe wall, and is denoted in FIG. 7 as wall coupon corrosion rate.

Figure 7:
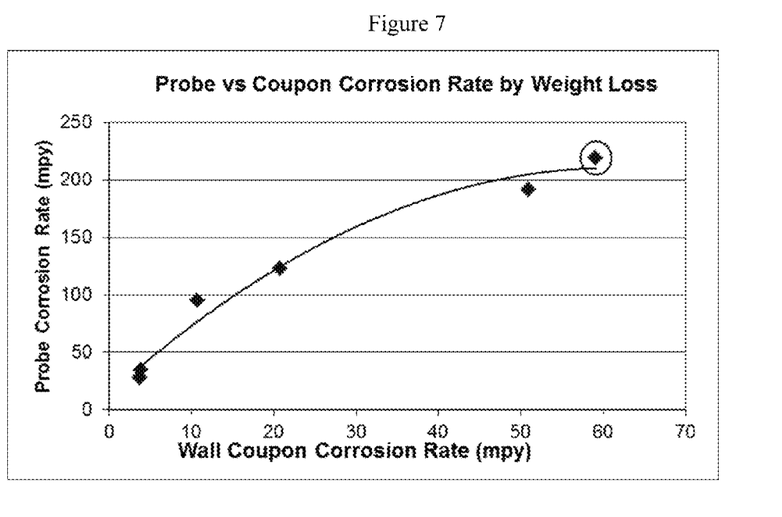
FIG. 7 plots the weight loss corrosion rate (mils per year) of the mechanical oscillator metal loss sensor under flowing conditions compared to the corrosion rate of a coupon flush with the pipe wall (both high and low corrosion rates).

Each of the data points in FIG. 7 is based on a test period of approximately 1 week and different corrosion rates are achieved by adjusting the available oxygen in the water. The circled data point in FIG. 7 corresponds to the test results shown in FIG. 6. For all of the data shown in FIGS. 6 and 7, corrosion probe [140] in FIG. 1 was always inserted into the flow loop facility at a fixed depth and consistent orientation. Maintaining a fixed position orientation during the calibration process is necessary so that the flow turbulence wall shear stress around the probe is consistent. As subsequently described, the higher corrosion rate at the probe compared to the pipe wall coupon is attributable to the higher turbulence around the probe. Within experimental measurement expectation, there is reasonable accord between the probe's average corrosion rate computed by mass loss (210 mpy) compared to the average corrosion rate determined by the resonance frequency change (207 mpy). The corrosion rate based on resonance frequency is calculated using the FIG. 6 rate of frequency change, the FIG. 5 calibration curve (physically a different probe), and Equation 3.

Equations 1-3 and the associated procedures enable a method to calibrate the frequency change of the mechanical oscillator metal loss probe to an absolute metal loss rate from the mechanical oscillator. However, as demonstrated by the FIG. 7 results, the metal loss rate from the corrosion sensor is not necessarily the same as the metal loss rate from the process containment elements (pipes vessels, and internal components). As shown in FIG. 1, the tuning fork type of corrosion sensor protrudes into the flowing fluid. In a flowing fluid environment, this protrusion causes more wall shear stress and turbulence on the stems of the mechanical oscillator than on the pipe wall. In some corrosion environments, a corrosion product may form a protective scale on the surface of the corroding component and subsequently provides protection from additional corrosion or corrosion form other sources. If the flowing fluid interferes with the formation of the protective scale or degrades its stability, then the flow parameters also contribute to the net corrosion rate of the surfaces. Mass transport of corrosion products to the metal surface will also be a function of the flow dynamics. In a fluid flowing environment, the corrosion rate at the stems of the mechanical oscillator may not be the same as the corrosion rate at the pipe or vessel wall, particularly for the situation where corrosion product (scale) is likely to form.

Figure 8:
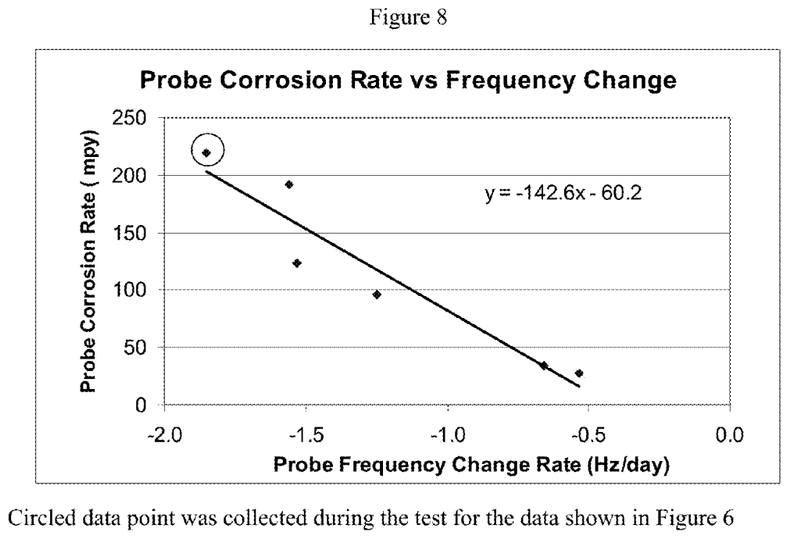
FIG. 8 plots the metal loss sensor corrosion rate data from FIG. 7 as a function of the metal loss sensor frequency change per day.

From FIG. 7, the relationship between the mechanical oscillator and pipe wall corrosion rates can be determined by relating the weight loss of the mechanical oscillator inside the process unit to the weight loss of a coupon on an interior wall of the process unit. Relating the frequency rate change of the probe to the corrosion rate at the probe is shown in FIG. 8. The FIG. 8 data were collected during the same tests that were used to compute the FIG. 7 weight loss results. The vertical axis of both FIGS. 7 and 8 presents the corrosion rate of the probe as determined by weight loss. The horizontal axis of FIG. 8 is a measure of the corresponding rate of frequency change that occurred on the probe during each test. That rate of frequency change for each point in FIG. 8 is derived from a test producing a plot similar to the one shown in FIG. 6.

Figure 9:
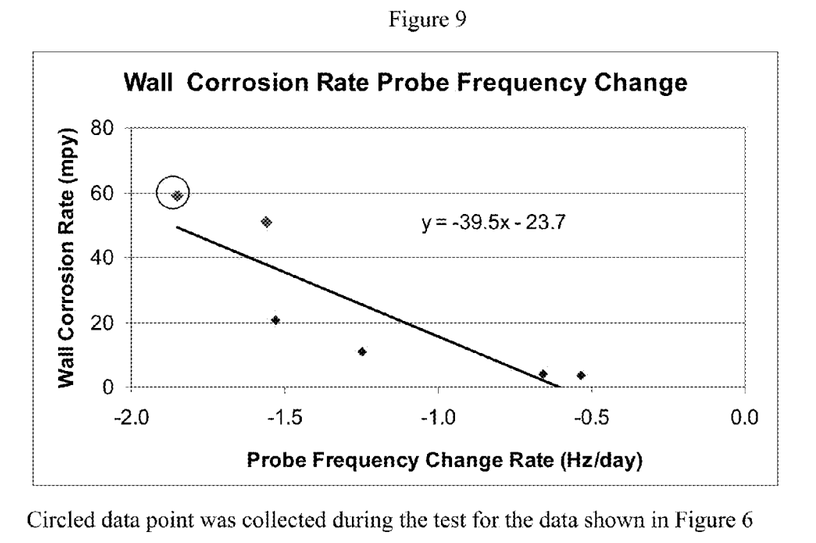
FIG. 9 plots the wall coupon metal loss corrosion rate (mils per year) during the FIG. 8 testing as a function of the metal loss sensor frequency change per day.

As noted previously, the fluid flow conditions at the probe may cause the corrosion rate at the probe to be different than the corrosion rate at the pipe wall pressure containment boundary. Typically, the corrosion rate of interest is the corrosion rate at the pipe wall rather than the corrosion rate of the probe. FIG. 9 enables computation of the corrosion rate at the pipe wall directly by measuring the rate of frequency change of the metal loss probe. FIG. 9 is derived from FIG. 8 by substituting the wall coupon corrosion rates shown in FIG. 7 for the corresponding probe corrosion rates shown in FIG. 8. The implicit assumption for this procedure is that the corrosion rate of the flush mounted coupon [120] of FIG. 1 is the same as the corrosion rate at an adjacent pipe pressure boundary.

Computational fluid dynamics (CFD) has been used to compute the wall shear stress for situations using the tuning fork mechanical oscillator similar to the one described FIG. 2. An off-the-shelf CFD model (ANSYS Fluent, 275 Technology Drive, Canonsburg, Pa. 15317) based on the Navier-Stokes equation has been used to simulate the single—phase flow through the pipe and around the probe. The CFD methodology employed has been validated by the vendor for a variety of standard single-phase flow problems. CFD computations require that explicit dimensions and flow parameters be used when calculating wall shear stress. To obtain accurate results, care was taken to sufficiently resolve the surfaces of the probe and the pipe according to the vendor recommendations. In the example that follows, the following details are used in the calculation process:

Where:
$\rho$=fluid density=1000 kg/m$^3$ (water)
$\mu$=absolute viscosity=1 cP (water)
u=fluid velocity=0.55 m/sec
Dpipe=internal diameter of the pipe=100 mm
DHstem=diameter of the corrodible stem element=4.8 mmm
Lpipe=downstream distance from the probe where the wall shear stress on the pipe is calculated (up to 1.3 m-13 pipe diameters)
Re=Reynolds number as determined at the pipe wall or probe stems A power-law relationship between corrosion rate and shear stress was developed by Efird, Wright, Boros and Hailey (Efird, K. D.; Wright, E. J.; Boros, J. A.; Hailey, T. G.; "Correlation of Steel Corrosion in Pipe Flow with Jet Impingement and Rotating Cylinder Tests" Corrosion 49 (1993) 992-1003). This relationship is shown by $$R_{corr}=a\tau_w^b \qquad \text{Equation 4}$$

In the above equation, $R_{corr}$ is the rate of corrosion in mils/yr and $\tau_w$ is the wall shear stress in N/m$^2$, while the coefficient (a) and exponent (b) on $\tau_w$ account for the effects of solution chemistry. For constant process and solution conditions (e.g., temperature, concentration and type of corrosive species, etc.) one can use this equation to compare the corrosion rates of various surfaces. The absolute corrosion rates for each surface can be calculated (using the Equation 4), or relative corrosion rates can be calculated using ratios of the above equation, shown below:

$$R_{corr\ surface\ A}/R_{corr\ surface\ B}=\tau_{wA}^b/\tau_{wB}^b \qquad \text{Equation 5}$$

Where
$R_{corr\ surface\ A}$=corrosion rate of surface A (mils/yr)
$R_{corr\ surface\ B}$=corrosion rate of surface B (mils/yr)
$\tau_{wA}$=wall shear stress of surface A (N/M$^2$)
$\tau_{wB}$=wall shear stress of surface B (N/m$^2$)

In this manner it is possible to relate the corrosion rate of surface A (the mechanical oscillator) as a percentage of the corrosion rate of Surface B (the pipe wall). This situation is the case for the mechanical oscillator corrosion sensor [140] and the pipe wall coupon [110, 120]. The only difference in conditions relevant for corrosion between the walls of the sensor and the walls of the pipe to be measured is the turbulence causing wall shear stress at each location. Consequently, Equation 4 parameters (a) and (b) are the same at the corrosion sensor and the pipe wall.

Corrosion in pipes due to a flowing medium is a complex phenomenon that involves mass transfer through the boundary layer from and to the flow medium, as well as mass transfer through the developing scale or corrosion products layer at the pipe wall. Correlating corrosion rate with the shear stress at the pipe wall, assumes that the mass transfer at the flowing medium boundary layer is controlled by the prevalent hydrodynamics. It is expected that the exact coefficients of the correlating relationship depend on the mass transfer through the developing scale. In particular, it is expected that at low corrosion rates, the mass transfer through the boundary layer is controlling, while at higher corrosion rates a complex interplay between the mass transfer through the boundary layer and the mass transfer through the developing scale will take place, and the controlling step will depend on the particular chemistry and identity of the developing scale.

Figure 10A:
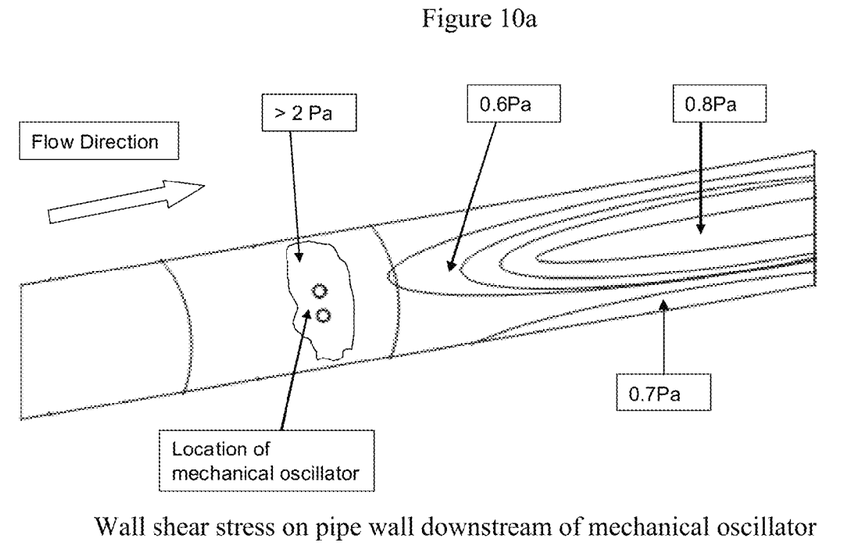
FIGS. 10a/b respectively present the wall shear stress calculated from computational fluid dynamics on piping downstream of the mechanical oscillator and in the vicinity of an elbow for a fixed liquid flow velocity with no influence from the mechanical oscillator.
Figure 10B:
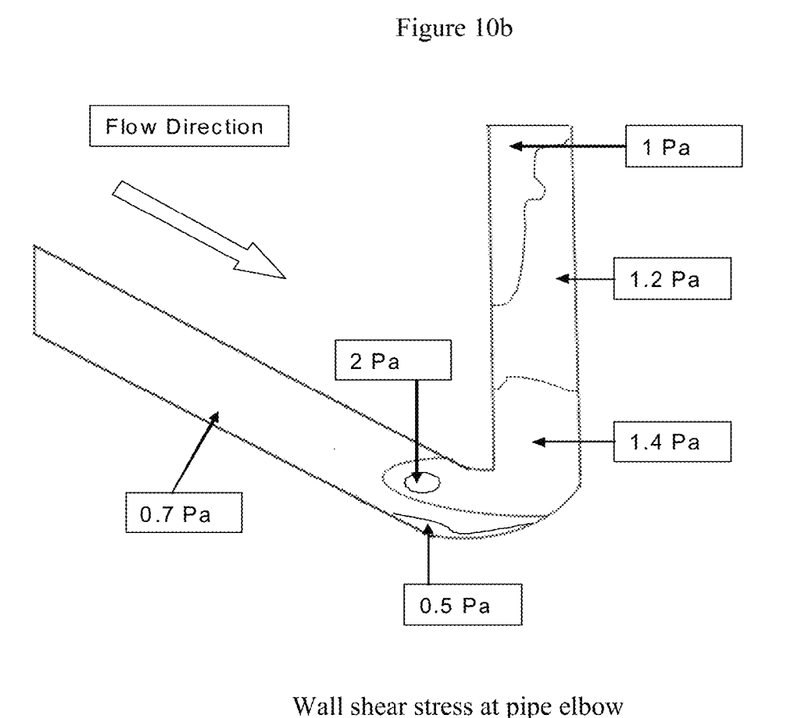

Notwithstanding the complexities of the CFD wall shear stress analysis, the results of FIG. 7 are consistent in the anticipation of higher corrosion rates at the mechanical oscillator compared to the pipe wall. The flow disturbances from the mechanical oscillator cause an increase in turbulence at the corrodible element compared to the turbulence at the pipe wall. FIGS. 10a/b show the CFD results to compute the wall shear stress on a) straight pipe at and downstream of the mechanical oscillator corrosion probe shown in FIG. 2 (average 0.5-0.6 Pascals upstream of the probe); and b) the pipe wall at an elbow with a bend radius of 1.5 pipe diameters (maximum 2 Pascals). The increased wall shear stress at the corrodible section of the FIG. 2 mechanical oscillator (average of 27 Pascals) is consistent with the higher corrosion rate shown in FIG. 7 for the probe stems compared to the flush-mounted wall coupon. The maximum wall shear stress determined by CFD at the edge of the corrodible element is 32 Pascals.

Any set of corrosion rate data from the FIG. 7 test would enable solving for the parameters a and b in Equation 4 using the corresponding wall shear stresses for the mechanical oscillator and the pipe wall. Because of the aforementioned complexities of mass transfer through boundary layers and scale, it would not be expected that there will be unique values for parameters (a, b) in Equation 4 over the aforementioned range of corrosion rates and oxygen concentrations. The following table shows that the computed values of (a, b) cover a wide range. However, over that entire range, the ratio of mechanical oscillator corrosion rate (as determined by mass loss) to the elbow corrosion rate (estimated using Equations 4 and 5 for the straight section wall shear stress of 0.6 Pascals and elbow wall shear stress of 2 Pascals) is bounded to within a factor of 2. Notwithstanding this wide range of corrosion conditions (such as oxygen concentration and pH), knowing the corrosion rate at the mechanical oscillator enables a bounded estimate of the corrosion rate at the elbow without physically having a probe at the elbow. For the case where the chemical composition of the corrosion environment is more tightly defined, the elbow corrosion rate can be accurately predicted knowing the measured corrosion rate at the mechanical oscillator. As the data in the table demonstrate, the three examples with the highest corrosion rates provide a consistent ratio between the tuning fork probe and elbow corrosion rates. Similarly, the 3 lowest corrosion rates also provide consistent ratios. The mechanical oscillator corrosion probe calibration and application of CFD methods described herein enable a means to assess corrosion rates throughout a piping system with one or few physical corrosion rate sensors installed.

| Mechanical Oscillator Corrosion Rate (mpy) | Wall Coupon Corrosion Rate (mpy) | Equation 4 parameter (b) | Equation 4 parameter (a) | CFD Elbow Corrosion Rate for Wall Shear Stress = 2 Pascals | Ratio:Oscillator mpy (via weight loss) to Elbow mpy (CFD based) |
|---|---|---|---|---|---|
| 191.9 | 50.9 | 0.35 | 60.84 | 77.5 | 2.5 |
| 219.5 | 59.1 | 0.34 | 70.51 | 89.5 | 2.5 |
| 209.5 | 54.8 | 0.35 | 65.63 | 83.8 | 2.5 |
| 122.8 | 20.8 | 0.47 | 26.40 | 36.5 | 3.4 |
| 95.3 | 10.8 | 0.57 | 14.43 | 21.5 | 4.4 |
| 34.3 | 3.9 | 0.57 | 5.17 | 7.7 | 4.5 |
| 27.8 | 3.7 | 0.53 | 4.88 | 7.0 | 4.0 |

Note for the above table: the corrosion rates in the first 2 table columns are determined by standard weight loss measurements. The CFD elbow corrosion rate computation is made using Equation 4, with wall shear stress at the elbow, $\tau_w$, set to 2 Pascals. Parameters "a" and "b" are determined from the average wall shear stress (27 Pascals) at the corrodible element and a wall shear stress at the pipe wall coupon of 0.6 Pascals. The column labeled "CFD Elbow Corrosion Rate for Wall Shear Stress=2 Pascals" is determined from Equation 4. The "Ratio" column is computed as the quotient of the first and fifth columns. The Equation 4 parameters (a) and (b) do vary as a function of the corrosive medium (temperature, density, chemical composition). However, it is assumed that they are the same at the corrosion sensor and the pipe wall coupon with the context of a given test (e.g. for a given row in the table).

What is claimed is:

1. A method for determining the amount of corrosion which has occurred on an interior surface of a process unit due to a corrosive fluid comprising:
    (a) providing a corrosion sensor that is located within the process unit; wherein the corrosion sensor is a metal loss sensor, an electrical resistance sensor, or a linear polarization sensor;
    (b) exposing the corrosion sensor to a corrosive fluid within the process unit;
    (c) determining the corrosion that has occurred on the corrosion sensor, and
    (d) relating the corrosion of the corrosion sensor to the amount of corrosion which has occurred on at least one point on a surface of the process unit; wherein the at least one point on a surface of the process unit is at a point other than where the corrosion sensor is located and wherein the at least one point on a surface of the process unit is an interior wall of a pressure containment boundary; wherein the relating of the corrosion on the corrosion sensor to the corrosion on the process unit comprises;
    (i) determining a corrosion rate of the corrosion sensor;
    (ii) determining a corrosion rate at the at least one point on a surface of the process unit; wherein the determining the rate of corrosion at the at least one point on a surface of the process unit comprises determining the rate of corrosion as a function of shear stress at the at least one point; and
    (iii) calculating a ratio of the corrosion rate of the corrosion sensor to the corrosion rate at the at least one point on a surface of the process unit.

2. The method of claim 1 wherein said one point is an interior wall of a pipe.

3. The method of claim 1 wherein said corrosion sensor is a mechanical oscillator.

4. The method of claim 3 wherein said corrosion sensor is a tuning fork having a resonance frequency.

5. The method of claim 1 wherein said corrosion sensor outputs an electrical signal.

6. The method of claim 1 wherein the method is corrected for scale forming on the corrosion sensor.

7. The method of claim 1, wherein the determining the corrosion that has occurred on the corrosion sensor includes comparing the metal loss on the corrosion sensor to a non-corroding reference probe.

* * * * *